(12) United States Patent
Zhuang et al.

(10) Patent No.: US 12,426,794 B2
(45) Date of Patent: Sep. 30, 2025

(54) PULSE WAVE CONDUCTION PARAMETER MEASURING METHOD AND PULSE WAVE CONDUCTION PARAMETER PROCESSING DEVICE

(71) Applicant: SHENZHEN DARMA TECHNOLOGY CO., LTD., Shenzhen (CN)

(72) Inventors: Shaochun Zhuang, Shenzhen (CN); Fei Ye, Shenzhen (CN)

(73) Assignee: CARDIOSTORY INC., Lewes, DE (US)

( * ) Notice: Subject to any disclaimer, the term of this patent is extended or adjusted under 35 U.S.C. 154(b) by 754 days.

(21) Appl. No.: 17/051,335

(22) PCT Filed: Apr. 28, 2018

(86) PCT No.: PCT/CN2018/085203
§ 371 (c)(1),
(2) Date: Oct. 28, 2020

(87) PCT Pub. No.: WO2019/205175
PCT Pub. Date: Oct. 31, 2019

(65) Prior Publication Data
US 2021/0127991 A1 May 6, 2021

(51) Int. Cl.
*A61B 5/0285* (2006.01)
*A61B 5/00* (2006.01)
(Continued)

(52) U.S. Cl.
CPC ........ *A61B 5/0285* (2013.01); *A61B 5/02125* (2013.01); *A61B 5/0261* (2013.01);
(Continued)

(58) Field of Classification Search
CPC . A61B 5/0285; A61B 5/02125; A61B 5/0261; A61B 5/6823; A61B 2562/0219; A61B 2562/0238; A61B 2562/0266
See application file for complete search history.

(56) References Cited

U.S. PATENT DOCUMENTS

2005/0124864 A1\* 6/2005 Mack .................. A61B 5/6892
600/587
2017/0360374 A1\* 12/2017 Elliott ................ A61B 5/02241
(Continued)

FOREIGN PATENT DOCUMENTS

CN 101849819 A 10/2010
CN 105916439 A 8/2016
(Continued)

*Primary Examiner* — Tse W Chen
*Assistant Examiner* — Joseph A Tombers
(74) *Attorney, Agent, or Firm* — Cheng-Ju Chiang

(57) ABSTRACT

The present invention provides a pulse wave conduction parameter measuring method and a pulse wave conduction parameter processing device. The method comprises: acquiring vibration information of a subject from one or more vibration-sensitive sensors configured to be placed at a predetermined position; generating hemodynamic related information on the basis of the vibration information; determining a first feature point and a second feature point in the hemodynamic related information, wherein the first feature point is a point related to an aortic valve opening time of the subject, and the second feature point is related to a pulse wave arrival time of the subject; and determining a pulse wave conduction time of the subject on the basis of the first feature point and the second feature point.

13 Claims, 6 Drawing Sheets

(51) Int. Cl.
*A61B 5/021* (2006.01)
*A61B 5/026* (2006.01)

(52) U.S. Cl.
CPC .... *A61B 5/6823* (2013.01); *A61B 2562/0219* (2013.01); *A61B 2562/0238* (2013.01); *A61B 2562/0266* (2013.01)

(56) References Cited

U.S. PATENT DOCUMENTS

2018/0042486 A1* 2/2018 Yoshizawa .......... A61B 5/02125
2020/0129078 A1* 4/2020 Kanegae .............. A61B 5/7253

FOREIGN PATENT DOCUMENTS

| | | |
|---|---|---|
| CN | 107072538 A | 8/2017 |
| CN | 107106054 A | 8/2017 |
| CN | 107126201 A | 9/2017 |
| WO | 2017/211866 A1 | 12/2017 |

* cited by examiner

PULSE WAVE CONDUCTION PARAMETER MEASURING METHOD AND PULSE WAVE CONDUCTION PARAMETER PROCESSING DEVICE

CROSS REFERENCE TO RELATED APPLICATIONS

The present application is a 35 U.S.C. § 371 National Phase conversion of International (PCT) Patent Application No. PCT/CN2018/085203, filed on Apr. 28, 2018, the disclosure of which is incorporated by reference herein. The PCT International Patent Application was filed and published in Chinese.

FIELD OF THE INVENTION

The present invention relates generally to the field of a pulse wave conduction parameter measurement, and particularly relates to a non-invasive pulse wave conduction parameter measurement system, method, computer readable storage medium, and the processing device.

BACKGROUND OF THE INVENTION

The description herein only provide background information related to the application, and do not necessarily constitute prior art.

Worldwide, cardiovascular and cerebrovascular diseases are an important cause of morbidity and death, and morbidity and death caused by cardiovascular and cerebrovascular diseases are related to arterial vascular diseases. For example, angina pectoris and myocardial infarction are related to coronary artery disease; stroke is related to cerebral artery disease, and intermittent claudication is related to lower extremity arterial disease. The two main types of arterial lesions include structural lesions and functional lesions. Structural lesions are manifested as vascular obstruction, such as atherosclerosis; and functional lesions are manifested as changes in vascular function, such as vascular sclerosis. While, the elasticity change of arterial wall is the cause of the occurrence and development of various cardiovascular events.

The cyclical contraction and relaxation of the heart can not only cause changes in the flow rate and flow of blood in arteries, but also generate pulse waves that propagate along the blood vessel wall. Pulse Wave Velocity (PWV) is related to the elasticity of arteries. Generally, the greater the stiffness of the blood vessel, the faster the pulse wave velocity. Therefore, the degree of arterial elasticity can be assessed by measuring the pulse wave velocity.

SUMMARY OF THE INVENTION

Technical Problem

The object of the present invention is to provide a pulse wave conduction parameter measurement method, system, computer readable storage medium, and pulse wave conduction parameter processing device capable of measuring the Pulse Wave Transit Time of a subject.

Technical Solutions

In a first aspect, a pulse wave conduction parameter measurement method provided in the present invention, comprises steps of:

acquiring vibration information of a subject from one or more vibration sensors configured to be placed in predetermined positions;

generating hemodynamic related information based on the vibration information;

determine a first feature point and a second feature point in the hemodynamic related information, where the first feature point is related to the aortic valve opening time of the subject, and the second feature point is related to the Pulse Arriving Time of the subject; and determining the Pulse Wave Transmit Time of the subject based on the first feature point and the second feature point.

In a second aspect, a computer-readable storage medium provided in the present invention, having a computer program stored thereon, which when being executed to perform steps of the pulse wave conduction parameter measurement method described above.

In a third aspect, a pulse wave conduction parameter processing device provided in the present invention, comprises: one or more processors; a memory; and one or more computer programs, wherein the one or more computer programs are stored in the memory, and configured to be executed by the one or more processors to perform the steps of the pulse wave conduction parameter measurement method described above.

In a fourth aspect, a pulse wave conduction parameter measurement system provided in the present invention, comprises:

one or more vibration sensors configured to be placed in predetermined positions to acquiring vibration information of a subject; and the pulse wave conduction parameter processing device described above, connected to the one or more vibration sensors.

Advantages

The aorta of the human body passes through the thoracic cavity and abdominal cavity of the body and is not a superficial artery. The traditional method of measuring the pulse wave conduction parameter of the superficial artery is not suitable for the measurement of the pulse wave conduction parameter of the aorta. In the present invention, the vibration information of the subject is obtained from one or more vibration sensors configured to be placed in predetermined positions; hemodynamic related information is generated based on the vibration information; a first feature point and a second feature point of the hemodynamic related information is determined, wherein the first feature point is a point related to the aortic valve opening time of the subject, and the second feature point is a point related to the Pulse Arriving Time of the subject. The Pulse Wave Transit Time of the subject can be obtained based on the first feature point and the second feature point, thereby Pulse Wave Velocity can be obtained, and used to evaluate the elasticity of the artery. Therefore, using the method for measuring human aortic pulse wave conduction parameters provided in the present invention, the measurement can be performed only needs the test subject to lie on the measurement device or wear the measurement device without direct contact; the measurement accuracy is high, simple to operate, can improve the comfort to the test subject, and can be applied to scenes such as hospitals and homes.

BRIEF DESCRIPTION OF THE DRAWINGS

In order to explain more apparent the technical solution of the embodiments of the present invention, a brief description to the drawings conjunct in the description of the embodiment is given below. Obviously, the drawings described below are used in only some embodiments of the invention. For those of ordinary skill in the art, without creative work, the present invention can also be applied to other similar embodiments based on these drawings. Unless it is obvious from the language environment or otherwise stated, the same reference numerals in the figures represent the same structure or operations.

DETAILED DESCRIPTION OF THE INVENTION

As used in the description and claims, the singular form "a", "an" and "the" include both singular and plural references unless the context clearly dictates otherwise. Generally, the term "comprising" or "comprises" is intended to mean the steps or elements that have been clearly identified, and these steps or elements do not constitute an exclusive list, and the method or device can also include other steps or elements.

Figure 1:
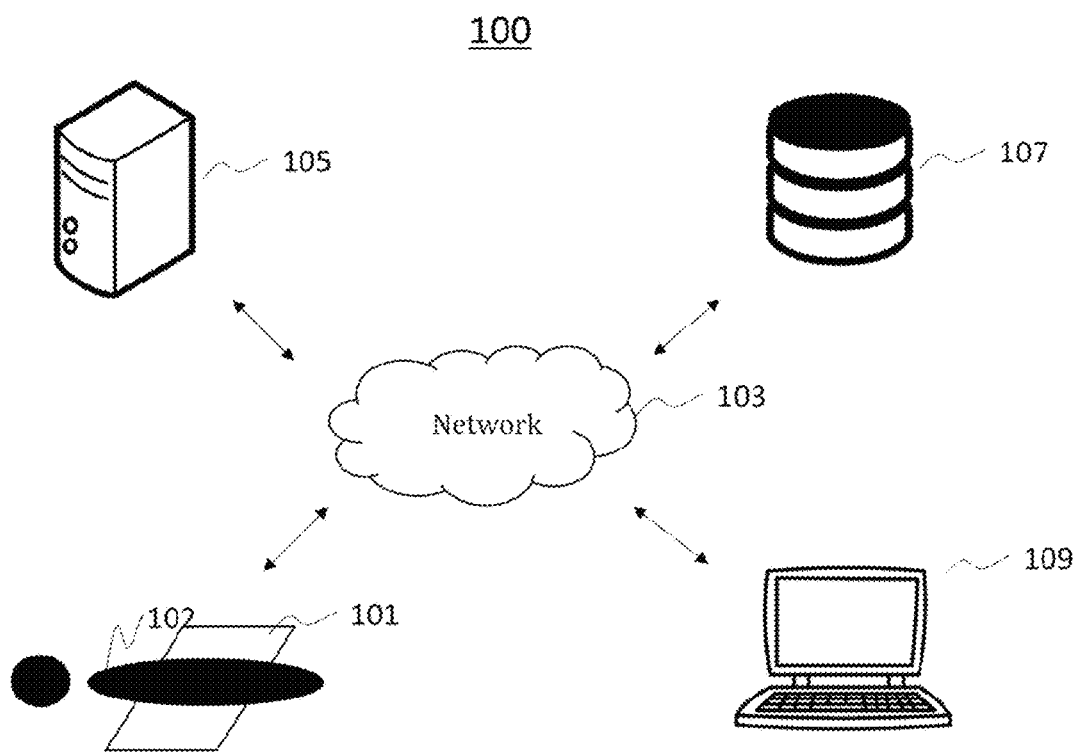
FIG. 1 is a schematic diagram of a pulse wave conduction parameter measurement system in accordance with some embodiments of the present invention.

FIG. 1 is a schematic diagram of a pulse wave conduction parameter measurement system 100 in some embodiments of the present invention. As shown in FIG. 1, the pulse wave conduction parameter measurement system 100 comprises a sensor device 101 and the pulse wave conduction parameter processing device 105 connected to the sensor device 101, and the pulse wave conduction parameter processing device 105 can be connected to the sensor device 101 through a network 103 or a signal transmission line.

The sensor device 101 can be configured to acquire vibration information of the subject 102. In some embodiments, the sensor device 101 can be a vibration sensor, such as one or more of: an acceleration sensor, a speed sensor, a displacement sensor, a pressure sensor, a strain sensor, a stress sensor, or sensors that convert physical quantities equivalently based on acceleration, speed, displacement, or pressure (such as electrostatic sensors, inflatable micromotion sensors, radar sensors, etc.). In some embodiments, the strain sensor can be an optical strain sensor. In some embodiments, the sensor device 101 can further include a temperature sensor, such as an infrared sensor, to obtain a body temperature of the subject. In some embodiments, the sensor device 101 can be configured as a rectangular; for example, the thickness is 3 mm, the length is 45 cm, and the width is 8 cm, or other suitable sizes. The sensor device 101 can be configured to be placed in various types of beds such as a medical bed or a nursing bed where the subject 102 is located. The subject 102 can be a vital body for vital signs monitoring. In some embodiments, the subject 102 can be a hospital patient or persons under care, such as an elderly person, a prisoner, or other people. The sensor device 101 can transmit the acquired vibration information of the subject 102 to the pulse wave conduction parameter processing device 105 through the network 103 or a signal transmission line for subsequent processing. In some embodiments, the vibration information obtained by the sensor device 101 can be processed to calculate the vital signs of the subject 102, such as heart rate, respiration rate, body temperature, and the like. In some embodiments, after processing the vibration information obtained by the sensor device 101, the pulse wave conduction parameters of the subject, such as the Pulse Wave Transit Time (PTT) and Pulse Wave Velocity PWV, can be calculated.

The pulse wave conduction parameter measurement system 100 provided in the embodiment of the present invention may further include an output device 109 connected to the sensor device 101 and/or the pulse wave conduction parameter processing device 105, and the sensor device 101 can transmit the vibration information to the output device 109 for output, for example, a waveform of the vibration information is displayed on a display.

The pulse wave conduction parameter measurement system 100 provided in the embodiment of the present invention can also include a storage device 107 connected to the sensor device 101 and/or the pulse wave conduction parameter processing device 105. The sensor device 101 may also transmit the acquired vibration information of the subject 102 to the storage device 107 for storage via the network 103. For example, the system 100 may include multiple sensor devices, and the vibration information of multiple subjects acquired by the multiple sensor devices can be transmitted to the storage device 107 for storage as part of customer data.

The network 103 can perform information exchange. In some embodiments, the components of the pulse wave conduction parameter measurement system 100 (that is, the sensor device 101, the network 103, the pulse wave conduction parameter processing device 105, the storage device 107, and the output device 109) can send or receive information between each other through the network 103. For example, the sensor device 101 can send the acquired vital signs of the subject 102 to the storage device 107 via the network 103 for storage. In some embodiments, the network 103 can be a single network, such as a wired network or a wireless network, or a combination of multiple networks. The network 103 can include, but is not limited to, LAN, WAN, a shared network, a dedicated network, and the like. The network 103 can include a variety of network access points, such as wireless or wired access points, base stations or network access points, through which other components of the pulse wave conduction parameter measurement system 100 can connect to the network 103 and send information via the network.

The pulse wave conduction parameter processing device 105 is configured to process information. For example, the pulse wave conduction parameter processing device 105 can receive the vibration information of the subject 102 from the sensor device 101, extract hemodynamic related signals from the vibration information, and further process the hemodynamic related signals to obtain the pulse wave conduction parameters of the subject 102. In some embodiments, the pulse wave conduction parameter processing device 105 can be a single server or a server group. The server group can be clustered or distributed (that is, the pulse wave conduction parameter processing device 105 can be a distributed system). In some embodiments, the pulse wave conduction parameter processing device 105 can be local or remote. For example, the pulse wave conduction parameter processing device 105 can access data stored in the storage device 107, the sensor device 101, and/or the output device 109 through the network 103. For another example, the pulse wave conduction parameter processing device 105 can be directly connected to the sensor device 101, the storage device 107, and/or the output device 109 for data storage. In some embodiments, the pulse wave conduction parameter processing device 105 can also be a cloud server, which can include, but is not limited to, public cloud, private cloud, hybrid cloud, and the like.

The storage device 107 is configured to store data and instructions. In some embodiments, the storage device 107 can include, but is not limited to, Random Access Memory, Read Only Memory, Programmable Read-Only Memory, and the like. The storage device 107 can be a device for storing information by means of electrical energy, magnetic energy, and optical means, such as hard disks, floppy disks, magnetic core memories, CDs, DVDs, and the like. The storage devices mentioned above are just some examples, and the storage device 107 is not limited to these. The storage device 107 can store the vibration information of the subject 102 acquired by the sensor device 101, and can also store data from the vibration information processed by the pulse wave conduction parameter processing device 105, such as vital signs (respiration rate, heart rate) of the subject 102. In some embodiments, the storage device 107 can be a component of the pulse wave conduction parameter processing device 105.

The output device 109 is configured to output data. In some embodiments, the output device 109 can output the vital signs after being processed by the pulse wave conduction parameter processing device 105, and the output manners include, but not limited to, graphics, text, data, voice or physical forms such as vibration or electric waves, such as one or more of: graphic display, digital display, voice broadcast, braille display, etc. The output device 109 can be one or more of: a display, a mobile phone, a tablet computer, a projector, a wearable device (watch, earphone, glasses, etc.), a braille display, and the like. In some embodiments, the output device 109 can display vital signs (such as respiration rate, heart rate, etc.) of the subject 102 in real time. In other embodiments, the output device 109 can display a report in non-real time, which is the measurement results of the subject 102 within the preset time period, such as the user's heart rate and the respiratory rate monitoring per minute during the sleeping period. In some embodiments, the output device 109 can also output early warning prompts, including but not limited to a sound alarm, a vibration alarm, and a screen display alarm, etc. For example, the subject 102 can be a patient being monitored, the output device 109 can be a display screen in a nurse's station, and the results displayed by the output device 109 can be real-time heart rate, real-time respiration rate, etc. When the heart rate or the respiration rate is abnormal (for example, exceeding a threshold or occurring a significant change during a preset time period), the output device 109 can emit an alarm sound to remind the medical staff, and the medical staff can rescue the patient in time. In other embodiments, the output device 109 can be a communication device (such as a mobile phone) carried by the doctor. When the vital signs of the subject 102 are abnormal, one or more output devices 109 carried by one or more doctors can receive the warning information, the warning information can be pushed according to the distance between the output devices 109 and the subject 102.

The pulse wave conduction parameter measurement system 100 described in the present invention can be applied to different scenarios, such as hospitals, health service centers, or homes. For example, the pulse wave conduction parameter measurement system 100 is used in a family scene, and the sensor device 100 can be placed on an ordinary family bed, when a subject 102 (such as an elderly person, a person suffering from a cardiovascular disease, a person in a postoperative recovery period) is sleeping at night, the sensor device 101 can acquire the vibration information of the subject continuously or in a preset manner, and then send the vibration information of the subject through the network 103 (the vibration information can be sent in real time, or at a preset time, for example, all the data from the previous night was sent the next morning) to the pulse wave conduction parameter processing device 105 for processing. The pulse wave conduction parameter processing device 105 can send the processed information (such as heart rate per minute, respiratory rate per minute, aortic PWV) to the terminal 109. The terminal 109 can be the computer of the family doctor of the subject 102, and the family doctor can evaluate the physical condition and rehabilitation of the subject 102 based on the processed information of the subject 102.

In some embodiments, the pulse wave conduction parameter processing device 105, the storage device 107 and the output device 109, which are components of the pulse wave conduction parameter measurement system 100, can be set in the same device or set in different devices. For example, the pulse wave conduction parameter measurement system 100 includes a sensor device 101 and a computer (the computing device 400 shown in FIG. 4). Where the sensor device 101 can be directly connected to a computer through a transmission line, or can be connected to a computer through a network. The computer can implement all the functions of the pulse wave conduction parameter processing device 105, the storage device 107, and the output device 109, and perform data processing, storage, display and other functions. In other embodiments, the pulse wave conduction parameter processing device 105, the output device 109, and the storage device 107 can be integrated into a whole. The sensor device 101, the pulse wave conduction parameter processing equipment 105, the output device 109 and the storage device 107 can also be set in a cushion.

Figures 2, 3:
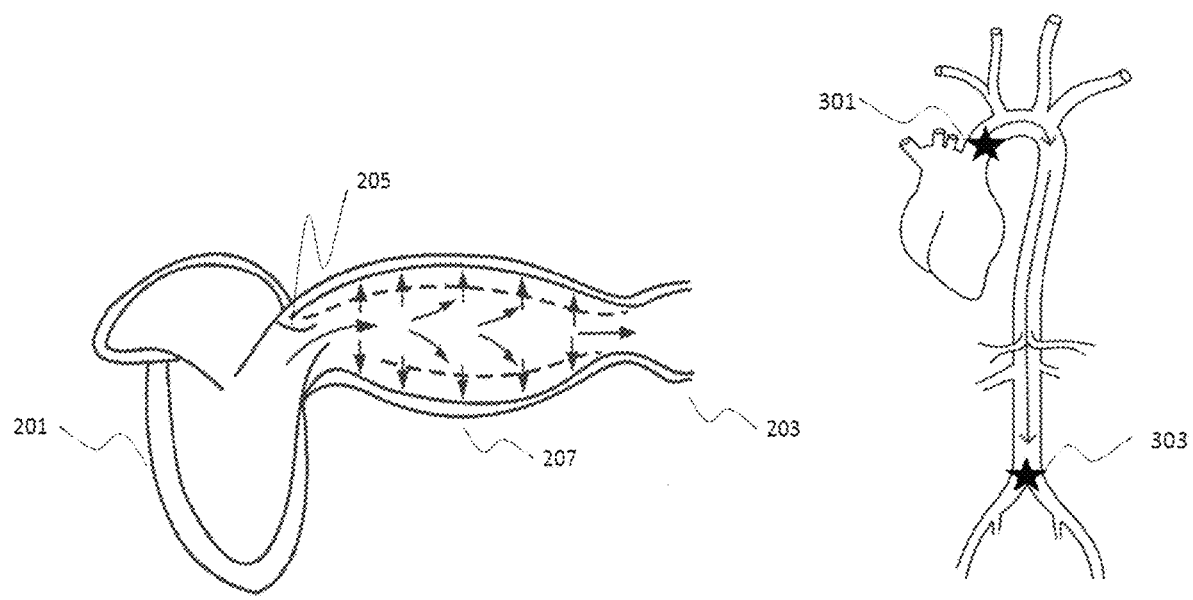
FIG. 2 is a schematic diagram of the principle of pulse wave generation.
FIG. 3 is a schematic diagram of the measurement principle of aortic pulse wave conduction parameters.

FIG. 2 is a schematic diagram illustrating the principle of pulse wave. As shown in FIG. 2, the left ventricle 201 and the aorta 203 are connected by the aortic valve 205. With the contraction of the left ventricle 201 to a certain pressure value, the aortic valve 205 opens (Aortic Valve Opening, AVO), and blood is injected from the left ventricle 201 into the aorta 203. Since the blood vessel is elastic, the blood will expand the aorta wall when injected into the aorta, and this pulse will propagate along the aortic wall, forming a pulse wave 207. Hemodynamics studies dynamics of blood flow in the cardiovascular system. It is based on blood flow and blood vessel wall deformation. The generation and propagation of pulse waves are related to blood flow and blood vessel wall deformation, which relates to hemodynamic research. The velocity of the pulse wave 207 along the aorta is related to the elasticity of the aorta 203, therefore, the Pulse Wave Velocity PWV can be used to assess the degree of vascular stiffness.

FIG. 3 is a schematic diagram of the measurement principle of aortic pulse wave conduction parameters. As shown in FIG. 3, the aorta can be divided into ascending aorta, aortic arch, and descending aorta. The ascending aorta starts from the aorta of the left ventricle and continues to the aortic arch obliquely to the upper right side. The brachiocephalic artery, the left common carotid artery, and the left subclavian artery arise from the aortic arch; and the brachiocephalic artery are divided into the right common carotid artery and the right subclavian artery behind the right sternoclavicular joint. The aortic arch is connected to the ascending aorta, arched at the back of the sternum stem to the left and rear, and the arch is moved to the left and back to the lower border of the fourth thoracic vertebra as the descending aorta. The descending aorta is the longest segment of the aorta. It splits into the left and right common iliac arteries at the fourth lumbar vertebra. It can be seen that the pulse wave of the aortic segment starts from the aortic origin 301 and is conducted along the aorta to the bifurcation 303 of the aorta and the left and right common iliac arteries. Therefore, the distance along the aorta path from the aorta origin to the bifurcation 303 of the aorta and the left and right common iliac arteries is taken as the aortic pulse wave conduction distance, the time for the pulse wave propagating from Point 301 to Point 303 is taken as the aortic Pulse Wave Transit Time, and the ratio of the aortic pulse wave conduction distance to the conduction time is taken as the aorta Pulse Wave Velocity (aortic PWV, aPWV).

Figure 4:
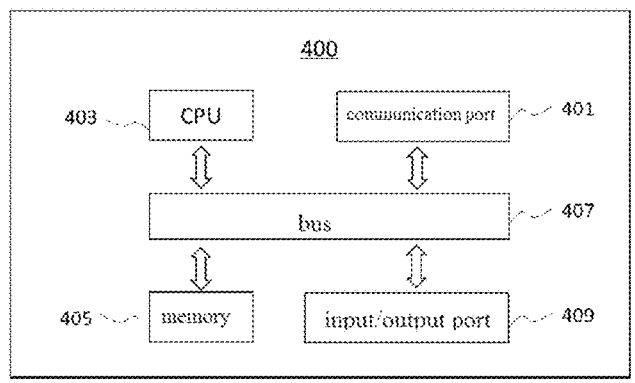
FIG. 4 is a block diagram of a computing device in accordance with some embodiments of the present invention.

FIG. 4 is a block diagram of a computing device 400 in some embodiments of the present invention. In some embodiments, the pulse wave conduction parameter processing device 105, the storage device 107, and/or the output device 109 of FIG. 1 can be implemented by the computing device 400. For example, the pulse wave conduction parameter processing device 105 can be implemented by the computing device 400 and configured to perform the functions of the pulse wave conduction parameter processing device 105 described in this invention. In some embodiments, the computing device 400 can be a dedicated computer. For ease of description, only one pulse wave conduction parameter processing device 105 is shown in FIG. 1. For those of ordinary skill in the art, it should be understood that calculation functions related to pulse wave conduction parameter measurement can also be implemented by multiple computing devices 400 with similar functions so as to distribute the calculation load.

The computing device 400 can include a communication port 401, a processor (Central Processing Unit, CPU) 403, a memory 405, and a bus 407. The communication port 401 is configured to perform data transmission with other devices through a network or a transmission line. The processor 403 is configured to perform data processing. The memory 405 is used for storing data and instructions, and the memory 405 can be a read-only memory ROM, a random read memory RAM, a hard disk, and other forms of memory. The bus 407 is configured to perform data communication in the computing devices 400. In some embodiments, the computing device 400 can further include an input/output port 409, which is configured to support data input and output. For example, other personnel can use an input device (such as a keyboard) to input data to the computing device 400 through the input/output port 409. The computing device 400 can also output data to an output device such as a display through the input/output port 409.

It should be understood that, for easy of description, only one processor 403 is described here. It should be understood that the computing device 400 can include multiple processors, and the operations or methods executed by one processor 403 can be jointly or separately executed by multiple processors. For example, one processor 403 described in the present invention can perform step A and step B. It should be understood that step A and step B can be performed jointly or separately by multiple processors. For example, the first processor performs step A, and the second processor performs step B, or the first processor and the second processor jointly perform steps A and B.

Figure 5A:
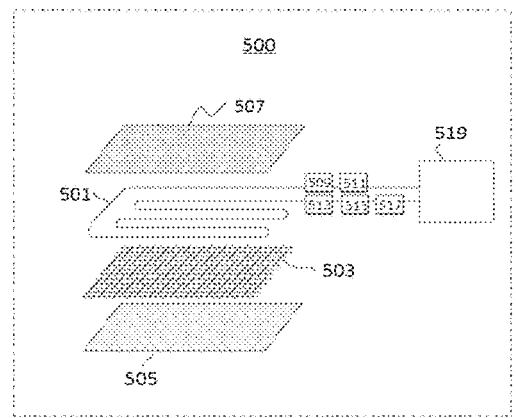
FIG. 5a is a schematic diagram of a sensor device in accordance with some embodiments of the present invention.

FIG. 5a is a schematic diagram of fiber-optic sensor device 500 according to some embodiments of the present invention. As shown in FIG. 5a, the fiber-optic sensor device 500 is a fiber-optic strain sensor, and includes an optical fiber 501, a mesh layer 503, a lower cover 505, and an upper cover 507. Where one end of the optical fiber 501 is coupled to a light source 509, which can be an LED light source. The light source 509 is coupled to a light source driver 511, which is configured to control the switch and energy level of the light source. The other end of the optical fiber 501 is coupled to a receiver 513. The receiver 513 is configured to receive the optical signal transmitted through the optical fiber 501. The receiver 513 is coupled to an amplifier 515, and the amplifier 515 is coupled to an Analog-to-Digital Converter 517, which can convert the received optical signal into a digital signal. The light source driver 511 and the Analog-to-Digital Converter 517 are coupled to a control and processing module 519. The control and processing module 519 is configured for signal control and signal processing. For example, the control and processing module 519 can control the light source driver 511 to drive the light source 509 emitting light; and the control and processing module 519 can also receive data from the Analog-to-Digital Converter 517, process the data adapted for wireless or wired network data transmission so that the processed data can be transmitted via the wireless or wired network to other devices, such as the pulse wave conduction parameter processing device 105, the storage device 107, and/or the output device 109 in FIG. 1. The control and processing module 519 can also control the sampling rate of the Analog-to-Digital Converter 517 so that it has different sampling rates according to different requirements. In some embodiments, the light source driver 511, the receiver 513, the amplifier 515, the Analog-to-Digital Converter 517, and the control and processing module 519 can be combined into one module to perform all functions.

The optical fiber 501 can be a multi-mode optical fiber, or can be a single-mode optical fiber. The optical fibers can be arranged in various shapes, such as a serpentine structure, referring to the shape of 501 as shown in FIG. 5a. In some embodiments, the optical fibers 501 can be arranged in a U-shape. In some embodiments, the optical fibers 501 can be arranged in a looped structure. Referring to FIG. 5f, the looped structure 521 is formed by one optical fiber arranged into a plurality of equal-sized loops disposed substantially in one plane, where each loop within the looped structure is partially overlapping yet laterally offset from neighboring loops. Each of the loops can form a substantially parallelogram structure (such as a rectangle, a square, etc.) with rounded edges without sharp bends. In some embodiments, each of the loops forms a circle or other ellipse. In some other embodiments, each of the loops forms a matching irregular shape without sharp bending.

The mesh layer 503 is made of any suitable material with through openings arranged in a repeating pattern. In some embodiments, the meshes are formed of woven fibers, such as polymer fibers, natural fabric fibers, composite fabric fibers, or other fibers. When the fiber-optic sensor device 500 is placed under the subject's body, the subject will apply an outside force to the fiber-optic sensor device 500. The mesh layer 503 can disperse the outside force that would have been applied to a certain point of the fiber and distribute to around the point of the fiber. Micro-bending in the optical fiber 501 causes changes in the parameter (such as the intensity) of light transmitted in the optical fiber 501. The receiver 513 receives the residual light, and changes in the amount of light are processed and determined by the control and processing module 519. The amount of bending of the optical fiber 510 under the application of outside force depends on the applied force, the diameter of the optical fiber, the diameter of the mesh fiber, and the size of the openings in the mesh. By balancing these parameters of the diameter of the optical fiber, the diameter of the mesh fiber, and the size of the openings in the mesh, when the external office is applied, the optical fiber will bend in different amount, which makes the fiber-optic sensor device 500 have different sensitivity to the outside force.

The lower cover 505 and the upper cover 507 can be made of silicone material, and are configured to surround the optical fiber 501 and the mesh layer 503, which can protect the optical fiber 501, and can also disperse the outside force so that the outside force is distributed along the force application point. The lower cover 505, the optical fiber 501, the mesh layer 503, and the upper cover 507 can be laminated into a whole, for example, glued together with a silicone adhesive, so that the fiber-optic sensor device 500 forms a sensor pad. The width and/or length of the sensor pad can be changed according to different arrangements of the optical fibers. When the looped structure is used, the width of the sensor pad can be at least 6 cm, or other suitable sizes, such as 8 cm. The length can be between 30 cm and 80 cm, for example, the length of 45 cm can be suitable for most people. In some embodiments, the thickness of the sensor pad may be 5 mm, preferably, the thickness is 3 mm. In some embodiments, the width and length of the sensor pad can be other sizes, and sensors with different sizes can be selected according to different test subjects. For example, test subjects can be divided into groups according to ages, heights, and weights. Different groups corresponding to sensors with different sizes. In some embodiments, when the optical fiber adopts a U-shaped structure, the width of the sensor pad may be 1 cm.

In some embodiments, the fiber-optic sensor device 500 can further comprise an outer cover (not shown in FIG. 5a) enclosing the lower cover 505, the mesh layer 503, the optical fiber 501 and the upper cover 507. The outer cover can be made of oil-resistant and water-repellent materials, such as hard plastic. In other embodiments, the fiber-optic sensor device 500 can further comprise a support structure (not shown in FIG. 5a). The support structure can be a rigid structure, such as cardboard, hard plastic board, wood board, etc. The support structure can be placed between the optical fiber 501 and the upper cover 507 so as to provide a support for the optical fiber 501. When an outside force is applied to the optical fiber 501, the support structure can make the deformation of the optical fiber rebound faster and the rebound time shorter, so that the optical fiber can capture higher frequency signal.

When an outside force is applied to the fiber-optic sensor device 500, for example, placing the fiber-optic sensor device 500 under the lying human body, when the subject is at rest, the human body's respiration and heartbeat will cause the body to vibrate. The vibration of the body can cause the bending of the optical fiber 501. The bending of the optical fiber changes the parameters of the light traveling through the optical fiber, such as light intensity. The changes in an intensity of light after processing can be used to represent the body's vibration. The sampling frequency of the fiber-optic sensor device 500 can also be adjusted, and can be adjusted according to the vibration information that needs to be captured. For example, when the sampling frequency is 1 k, relatively high frequency vibration information can be obtained.

Figure 5B:
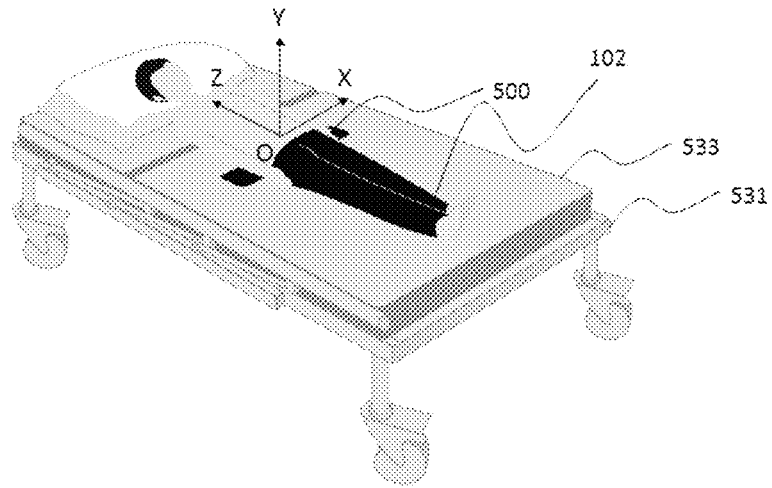
FIG. 5b is a schematic diagram of the placement position of the sensor device in accordance with other embodiments of the present invention.

FIG. 5b is a schematic diagram of the placement position of the sensor device according to some embodiments of the present invention. As shown in FIG. 5b, the fiber-optic sensor device 500 can be placed on the supporting bed 531. In other embodiments, there is a mattress 533 on the supporting bed 531, and the fiber-optic sensor device 500 can be placed on the mattress 533.

In order to clearly illustrate the positions and relationships of the body sections and the relationship between the positions of the sensor device and the body sections in the present invention, the anatomical coordinate system is introduced here. The standard anatomical position of the human body comprises an upright position and a supine position. Take the supine position as an example, as shown in FIG. 5b, the X-axis is the median horizontal axis, the Y-axis is the median sagittal axis, and the Z-axis is the median vertical axis. The origin O is located at the midpoint of the upper edge of the phalanx syndesmosis. The YZ plane is the median sagittal plane, which divides the human body into left and right sections, the XZ plane is the median coronal plane, which divides the human body into front and back sections, and the XY plane is the origin transverse plane, which divides the human body into upper and lower sections. The front, back, upper, lower, left, and right sections of the human body described in the present invention are described on the basis of the anatomical coordinate system.

The fiber-optic sensor device 500 can be placed at any position under the entire back region (including the back and waist) corresponding to the aorta of the subject 102; preferably placed at any position under the entire back region corresponding to the descending aorta (including the back and waist), that is, at any position under the entire back region of the body between the fourth thoracic vertebra and the fourth lumbar vertebra; and further preferably placed under the waist region, around the fourth lumbar vertebra and corresponding to the bifurcation of the descending aorta and the left and right common iliac arteries. In some embodiments, the shape and size of the fiber-optic sensor device 500 may be changed. For example, the fiber-optic sensor device 500 can be a cube with a side length of 10 cm and a thickness of 3 mm, or other suitable sizes. In some embodiments, the fiber-optic sensor device 500 may be set in the mattress as a whole. For example, the fiber-optic sensor device 500 can be fixed at a specific position on the mattress, and the mattress can be set with indicative means (such as by different colors, set with body contour lines, indicator lights, or convex and concave shapes, etc.) to indicate the lying position of the subject, so that the waist of the subject lies on the fiber-optic sensor device 500 when lying. The posture of the subject 102 can be supine, with the hands hanging down naturally beside the body or on the abdomen, the arms hanging down naturally, the legs being naturally straightened, the head straightened, relaxing spirit, and breathing naturally. In some embodiments, the subject 102 may also be prone. After the subject 102 is in a resting state, the fiber-optic sensor device 500 can start to continuously collect vibration signals.

Figure 5C:
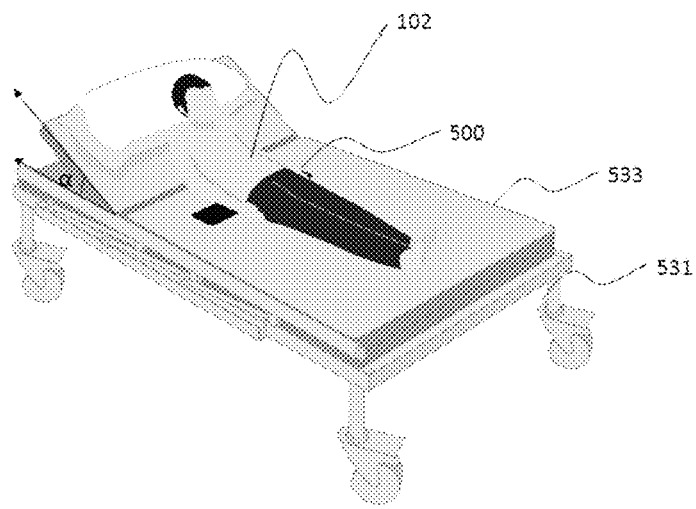
FIG. 5c is a schematic diagram of the placement position of the sensor device in accordance with other embodiments of the present invention.

FIG. 5c is a schematic diagram of the placement position of the sensor device according to other embodiments of the present invention. In some embodiments, for some subject 102 suffering from other diseases (such as asthma, cough, etc.), it is not suitable to lie down and supine to measure pulse wave conduction parameters. In this case, the support bed 531 can use a hospital rocking bed, can raise the upper part thereof so as to raise the upper body of the subject 102, and an inclination angle of the bed is a. When the subject 102 is in a lying-supine state and an upper body tilted state, the force applied to the fiber-optic sensor device 500 is different due to the action of the body's gravity, so the waveform of the obtained vibration information of the subject 102 is also different. When the inclination angle α of the bed is between 0 degrees and 60 degrees, although the acquired vibration waveforms are different, it has little effect on the calculation of the pulse wave conduction parameters and can be ignored or corrected with a correction coefficient. The preferred inclination angle of the bed is 0 degrees, that is, when the subject keeps in a lying-supine state, which is the preferable position for measuring pulse wave conduction parameters.

Figure 5D:
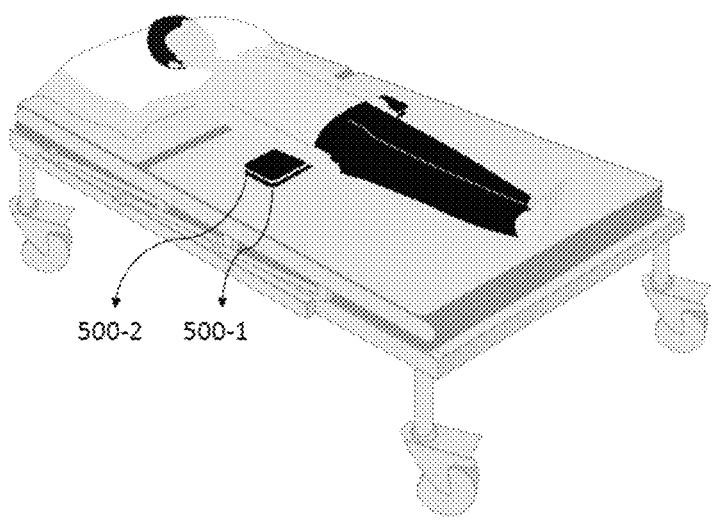
FIG. 5d is a schematic diagram of the placement position of the sensor device in accordance with other embodiments of the present invention.

FIG. 5d is a schematic diagram of the placement position of the sensor device according to other embodiments of the present invention. In some embodiments, two or more vibration sensors can be placed in the same position, as shown in FIG. 5d, two identical fiber-optic sensor devices 500 (500-1,500-2) can be stacked and placed under the lumbar region corresponding to the bifurcation of the descending aorta and the left and right common iliac arteries of a supine subject. In other embodiments, the size of the two or more vibration sensors may not be exactly the same. For example, one is an acceleration sensor with a smaller size, and the other is a fiber-optic strain sensor with a larger size, and the two sensors are placed in approximately the same positions; that is, the vibration information measured by the two sensors may include the vibration information of the same body section of the subject.

Figure 5E:
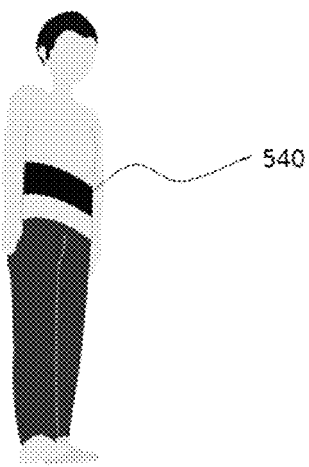
FIG. 5e is a schematic diagram of the placement position of the sensor device in accordance with other embodiments of the present invention.
Figure 5F:
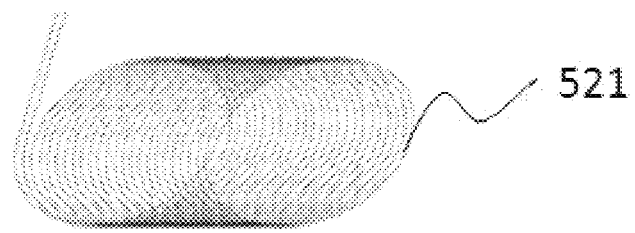
FIG. 5f is a schematic diagram of the arrangement of a looped structure of the optical fiber 501 in accordance with some embodiments of the present invention.

FIG. 5e is a schematic diagram of the placement position of the sensor device according to other embodiments of the present invention. In some embodiments, the vibration sensor can also be made into a human wearable device, such as a waist belt, as shown in FIG. 5e, and the wearable vibration sensor 540 can be a fiber-optic strain sensor, with a structure shown in FIG. 5a, where the upper cover 507 and the lower cover 505 can be made of soft and bendable material (such as silicone), and a shape of the vibration sensor 540 can be the same with a common waistband. In some embodiments, the vibration sensor can also be an acceleration sensor, can be a cube with a side length of 2 cm and a thickness of 1 mm, and can be attached to or wrapped in the waistband and worn by the test subject. The vibration sensor can be located at any position of the entire back region (including the back and waist) corresponding to the aorta, preferably located at any position of the entire back region (including the back and waist) corresponding to the descending aorta, that is, at any position of the entire body region between the fourth thoracic vertebra and the fourth lumbar vertebra, and more preferably at the position of the waist at the back of the body corresponding to the bifurcation of the descending aorta and the left and right common iliac arteries, that is, around the fourth lumbar vertebra.

The sensor device 101 may not be limited to the fiber-optic sensor device 500 and the wearable vibration sensor 540, and can be embodied in other forms such as clothes, mattresses, etc., so as to be suitable for other scenarios.

Figure 6:
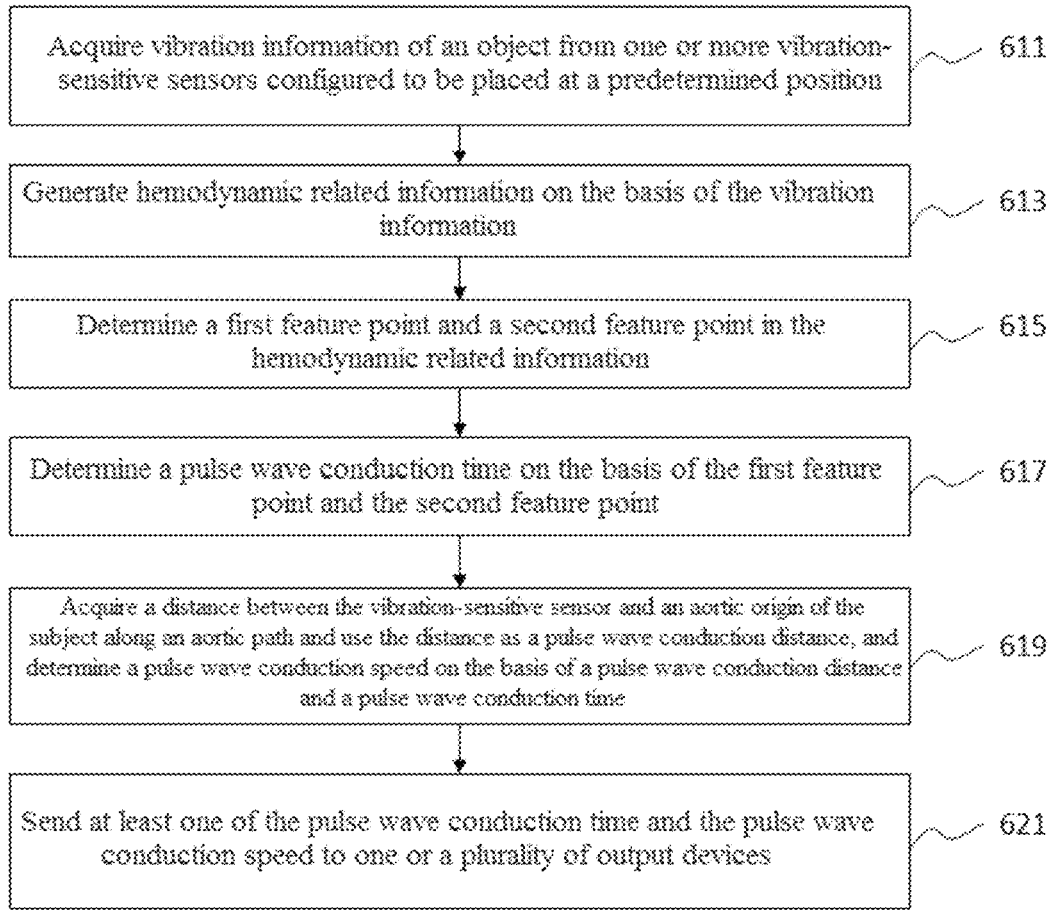
FIG. 6 is a flowchart of a pulse wave conduction parameter measurement method in accordance with some embodiments of the present invention.

FIG. 6 illustrates a flowchart of a pulse wave conduction parameter measurement method 600 in some embodiments of the present invention. In some embodiments, the method 600 can be implemented by the pulse wave conduction parameter measurement system 100 shown in FIG. 1. For example, the method 600 can be stored as an instruction set in the storage device 107 and executed by the pulse wave conduction parameter processing device 105. The pulse wave conduction parameter processing device 105 can be the computing device 400.

Figure 7:
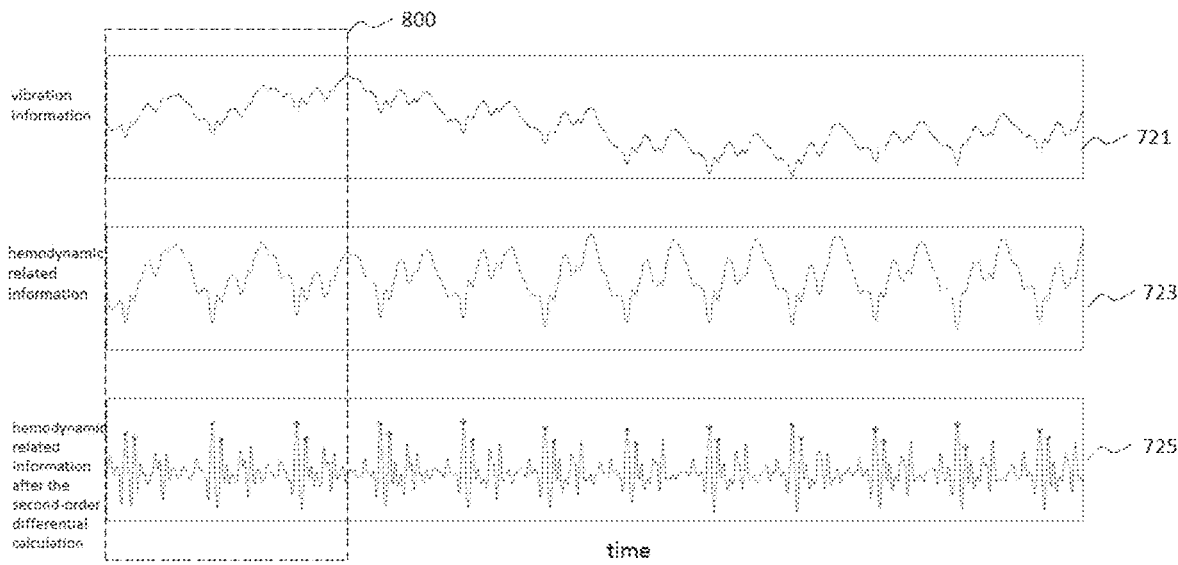
FIG. 7 is a signal waveform of one subject in accordance with some embodiments of the present invention.

Step 611: acquiring vibration information of the subject from one or more vibration sensors placed at predetermined positions. Step 611 can be executed by the processor 403. In some embodiments, the subject may be a hospital patient or persons under care, etc., and in a supine posture, as shown in FIG. 5b. The vibration sensor may be a fiber-optic sensor, for example, the fiber-optic sensor device 500 shown in FIG. 5a, with a cushion with a thickness of 3 mm, a width of 8 cm and a length of 45 cm, this size is suitable for the subjects with a normal body shape. The vibration sensors can be placed at any predetermined position under the entire back region (including back and waist) corresponding to the aorta; preferably placed at any position under the entire back region (including back and waist) corresponding to the descending aorta, that is, placed at any position under the entire body region between the fourth thoracic vertebra and the fourth lumbar vertebra; and further preferably placed at any position under the lumbar section corresponding to the bifurcation of the descending aorta and the left and right common iliac arteries, around the fourth lumbar vertebra. When the body shape of the subject is not within the normal range, for example, when the subject is too fat or too thin, the size of the fiber-optic sensor device 500 can be adjusted. For example, for a thin person, the length of the cushion can be shortened to at least equal to the body width of the subject, or a certain distance more, for example, about 5 cm more. Correspondingly, the length of the cushion can be lengthened for obese people. The fiber-optic sensor device 500 can obtain the vibration signal of the subject in real time and continuously. When the subject is in a supine resting state, the vibration sensors under the waist of the back region of the human body corresponding to the bifurcation of the descending aorta and the left and right common iliac arteries, can acquire vibration information including: body vibration information caused by breathing, body vibration information caused by contraction and relaxation of the heart, body vibration information caused by blood vessel wall deformation, and body movement information. Body vibration information caused by contraction and relaxation of the heart can include body vibration information caused by the contraction and relaxation of the heart itself, as well as body vibration information caused by blood flow caused by contraction and relaxation of the heart, such as body vibration information caused by blood flowing in the aortic arch due to heart's ejection. Body vibration information caused by blood vessel wall deformation, can be caused by pulse wave propagating along blood vessels, where heart's ejection causes the aortic wall to expand to form a pulse wave. The body movement information can be caused by the body movement such as leg bending, leg raising, turning over, shaking, etc. Specifically, breathing will cause the whole body, especially the body sections corresponding to the thorax and abdomen, to vibrate rhythmically. The contraction and relaxation of the heart will also cause the whole body, especially the body around the heart, to vibrate. The left ventricle pumps blood to the aorta, the blood will push against the aortic arch at the moment; and the heart itself and the connected large blood vessels as a whole will also undergo a series of movements. The farther the body part is from the heart, the weaker the vibration will be. The pulse wave propagating along the blood vessels will cause body vibration according to the blood vessels; the thinner the blood vessels and the farther away from the heart, the weaker the body vibration. The aorta is the largest artery in the human body, originating from the left ventricle of the heart and extending down to the thoracic cavity and abdomen. Therefore, when the vibration sensor is placed under the back or waist corresponding to the bifurcation of the descending aorta and the left and right common iliac arteries of the subject, body vibration information caused by breathing, body vibration information caused by heart contraction and relaxation, and body vibration information caused by blood vessel wall deformation are easier to capture. As shown in FIG. 7, the curve 721 is a waveform of the vibration information of a subject acquired by the fiber-optic sensor device 500 placed under the waist position of the back region of the body corresponding to the bifurcation of the descending aorta and the left and right common iliac arteries in an embodiment of the present invention. Where the horizontal axis represents time, and the vertical axis represents the first vibration information of the subject after normalization processing, which is dimensionless.

In some embodiments, the processor 403 may obtain vibration information of a supine subject from two vibration sensors placed at predetermined positions. For example, two fiber-optic sensor devices 500 can be stacked and placed at the same position, and the thickness of a single fiber-optic sensor device 500 can be only 3 mm, and then the two stacked fiber-optic sensor devices 500 will not increase the discomfort to the subject. The vibration sensors can be placed at any predetermined position under the entire back region (including back and waist) corresponding to the aorta; preferably placed at any position under the entire back region (including back and waist) corresponding to the descending aorta, that is, placed at any position under the entire body region between the fourth thoracic vertebra and the fourth lumbar vertebra; and further preferably placed at any position under the lumbar section corresponding to the bifurcation of the descending aorta and the left and right common iliac arteries, around the fourth lumbar vertebra. In other embodiments, multiple vibration sensors can be stacked and placed in the same position to obtain vibration information of the supine subject. For example, a plurality of fiber-optic sensor devices 500 may be stacked and placed, or fiber-optic sensor devices and acceleration sensor devices may be stacked. where multiple vibration sensors can be divided into two groups, and each group includes one or more sensors.

Step 613: generating hemodynamic related information based on the vibration information. Step 613 can be executed by the processor 403. In some embodiments, in step 611, when the subject is in a supine resting state, there is no body movement, and the sensor device 500 is placed under the waist region corresponding to the bifurcation of the descending aorta and the left and right common iliac arteries of the body. The vibration information acquired by the device 500 includes vibration information caused by breathing, vibration information caused by heart contraction, and vibration information caused by pulse wave propagating along blood vessels. Hemodynamics studies dynamics of blood flow in the cardiovascular system. It is based on blood flow and blood vessel wall deformation. The "hemodynamic related information" described in this invention refers to any information related to hemodynamics, which can include, but not limited to, one or more of: information related to blood flow generation (for example, heart's ejection caused by the contraction and relaxation of the heart), and blood flow-related information (such as cardiac output CO, left ventricular ejection impacting the aortic arch), blood pressure-related information (such as systolic arterial pressure, diastolic blood pressure, mean arterial pressure), or blood vessel-related information (For example, vascular elasticity). Pulse wave conduction parameters, such as Pulse Wave Velocity, are not only related to blood vessel elasticity, but also to the contraction and relaxation of the heart, and left ventricular ejection impacting the aortic arch. Therefore, the measurement of pulse wave conduction parameters involves a step of acquiring hemodynamic related information. In some embodiments, based on the vibration information acquired by the sensor device 500 in step 611, the hemodynamic related information to be generated by the processor 403 can comprise vibration information caused by left ventricular ejection impacting the aortic arch, and vibration information caused by blood vessel wall deformation (that's, vibration information caused by pulse wave propagating along blood vessels). In prior art, Ballistocardiogram (BCG) signal is used to represent periodic motions of the human body caused by heart beating. In body vibration information acquired by the vibration sensor described in the present invention, the body vibration information caused by the contraction and relaxation of the heart can also be expressed as a BCG signal. The hemodynamic related information described in the present invention includes BCG signals.

In some embodiments, the processor 403 may perform a series of processing on the acquired vibration information to generate hemodynamic related information. The vibration information acquired by the processor 403 include a variety of sub-vibration information (vibration information caused by breathing, vibration information caused by heart contraction, and vibration information caused by blood vessel wall deformation). The processor 403 can perform filtering in different frequency for different sub-vibration information. For example, the processor 403 can set the filtering frequency to below 1 Hz for filtering the vibration information caused by breathing, and the processor 403 performs filtering including but not limited to one or more of: low-pass filtering, band-pass filtering, IIR (Infinite Impulse Response) filtering, FIR (Finite Impulse Response) filtering, wavelet filtering, zero-phase bidirectional filtering, and polynomial fitting and smoothing filtering, where the vibration information can be filtered at least once. If the vibration information carries power frequency interference, a power frequency filter can used to filter power frequency noise. The processor 403 can filter the vibration information in the time domain or in the frequency domain. The processor 403 can also scale the filter vibration information according to the signal dynamic range to obtain hemodynamic related information. The curve 723 in FIG. 7 shows a time-domain waveform of hemodynamic related information generated by processor 403 processing the vibration information waveform 721 in an embodiment of the present invention, and the horizontal axis represents time.

Step 615: determining a first feature point and a second feature point in the hemodynamic related information. Step 615 can be executed by the processor 403. Where the first feature point can be used to represent the event of aortic valve opening. That is, when the contraction of the left ventricle reaches a certain pressure, the aortic valve opens, and blood is injected into the aorta and impacts the aortic arch. The time corresponding to the first feature point of the pulse wave propagating along the artery can be used as the starting of Pulse Wave Transit Time. The second feature point can be used to represent the pulse wave arrival event. When the vibration sensor is placed under the waist section corresponding to the bifurcation of the descending aorta and the left and right common iliac arteries of the test subject, the second feature point can represent the event that the pulse wave is conducted along the aorta to the bifurcation, and the time of second feature point can be used as the Pulse Arriving Time. In some embodiments, the hemodynamic related information generated by the processor 403 in step 613 may include the vibration information caused by the impact of the blood flow in the aortic arch when the left ventricle ejects blood, and the vibration information caused by the pulse wave propagating along the blood vessel. Where the aortic valve opens, the left ventricle ejects blood, and the time when the blood enters the aorta is considered to be the time point of pulse wave generation. At this moment, the blood flow ejected from the left ventricle will impact the aortic arch, causing the heart itself and the connected large blood vessels together to generate a series of movements, which causes displacement of the human body. Since the heart contracts and relaxes periodically, the displacement of the human body also changes periodically. This vibration information can be transmitted through the bones and muscles of the human body. The vibration sensor can capture this vibration information. Since the time delay between the event of the aortic valve opening and the event of the sensor capturing the corresponding body vibration information is usually small, about within 10 ms, the time delay can be ignored during pulse wave conduction parameter measurement; or, a correction coefficient can be used to correct the actually-measured aortic valve opening time. Therefore, the first feature point is related to the aortic valve opening time, and can be used to represent the event of aortic valve opening. The pulse wave is conducted along the blood vessel, and the vibration is also conducted along the blood vessel, which causes the human body to vibrate. Therefore, when the pulse wave reaches a certain position at the blood vessel, the vibration sensor under the body section corresponding to the certain position of the blood vessel can capture the vibration information. Similarly, the time delay between the Pulse Arriving Time and the time when the vibration sensor capturing the corresponding body vibration information is relatively small. This time delay can be ignored during pulse wave conduction parameter measurement; or, a correction coefficient can be used to correct the actually-measured Pulse Arriving Time. Therefore, the second feature point is related to the Pulse Arriving Time, and can be used to represent the event of the pulse wave arrival at the position. In the same cardiac cycle, the aortic valve opens after the left ventricle contracts to a certain pressure, and the blood impacts the aortic arch to generate pulse waves and cause body vibration. This vibration can be transmitted along the bones and muscles; and the vibration caused by the pulse wave propagates along the blood vessel; these two kinds of vibration can be captured by the vibration sensor successively.

In some embodiments, the first feature point and the second feature point can be obtained through a preset algorithm by the processor 403. For example, the processor 403 may perform the following steps to determine the first feature point and the second feature point.

Step A, obtaining the acceleration signal of the hemodynamic related information by the processor 403 processing the hemodynamic related information. In some embodiments, the vibration sensor is a fiber-optic strain sensor. When the fiber-optic strain sensor is placed under a supine subject, the optical fiber will be slightly deformed by force. The deformation of the optical fiber will cause changes in the parameter of the light propagating in the optical fiber, for example, changes in intensity of light. Therefore, the vibration signal captured by the fiber-optic strain sensor corresponds to the small displacement of the body, and the acceleration signal of the body vibration can be obtained by performing the second-order differential calculation on it. Specifically, the acceleration signal of hemodynamic related information can be obtained performing the second-order differential calculation on the hemodynamic related information. In some embodiments, the vibration sensor can be an acceleration sensor, and be able to capturing the acceleration signal. As shown in FIG. 7, the curve 725 is the time-domain waveform curve of the curve 723 after the second-order differential calculation, and the horizontal axis represents time.

Figure 8:
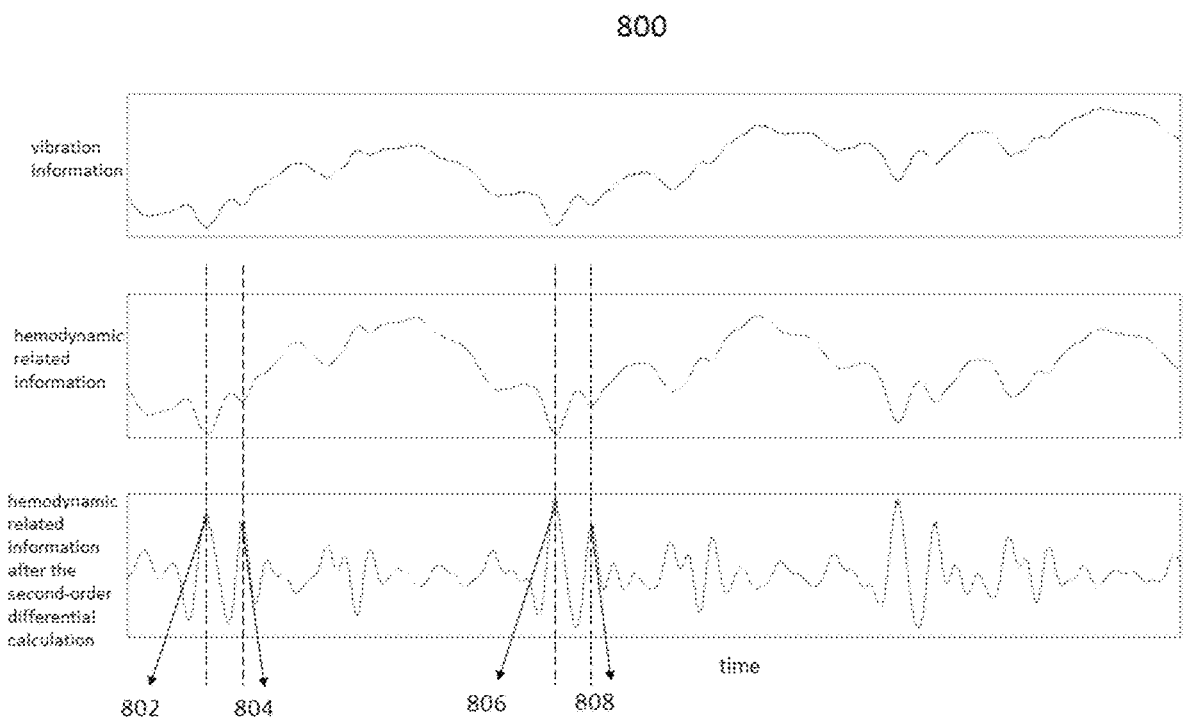
FIG. 8 is an enlarged view of the waveform in area 800 of FIG. 7.
Figure 9:
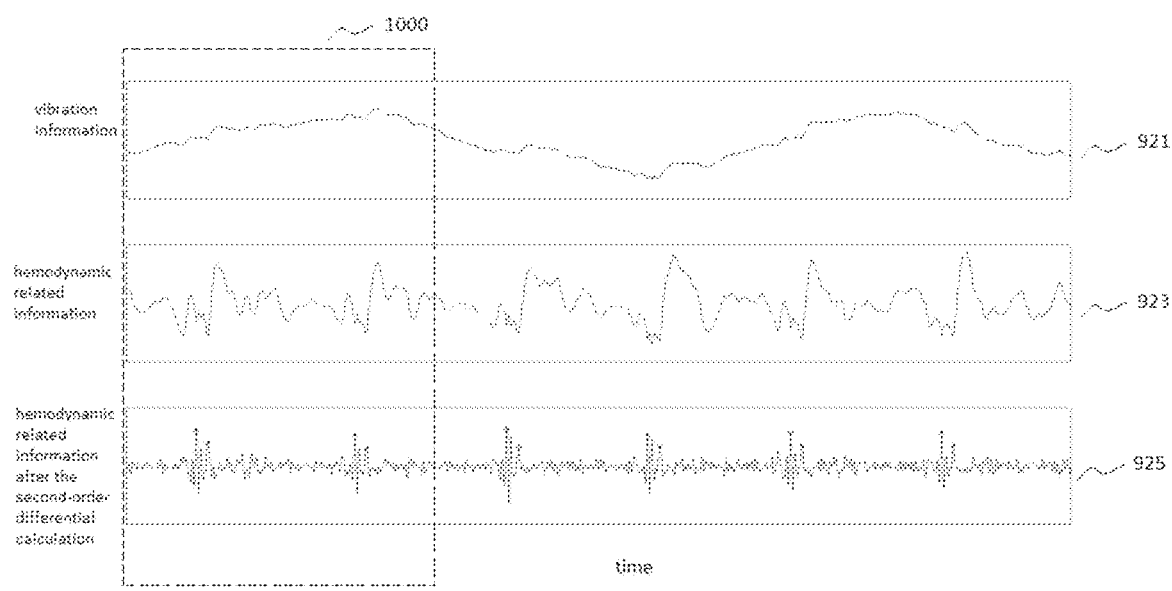
FIG. 9 is a signal waveform of another subject in accordance with some embodiments of the present invention.
Figure 10:
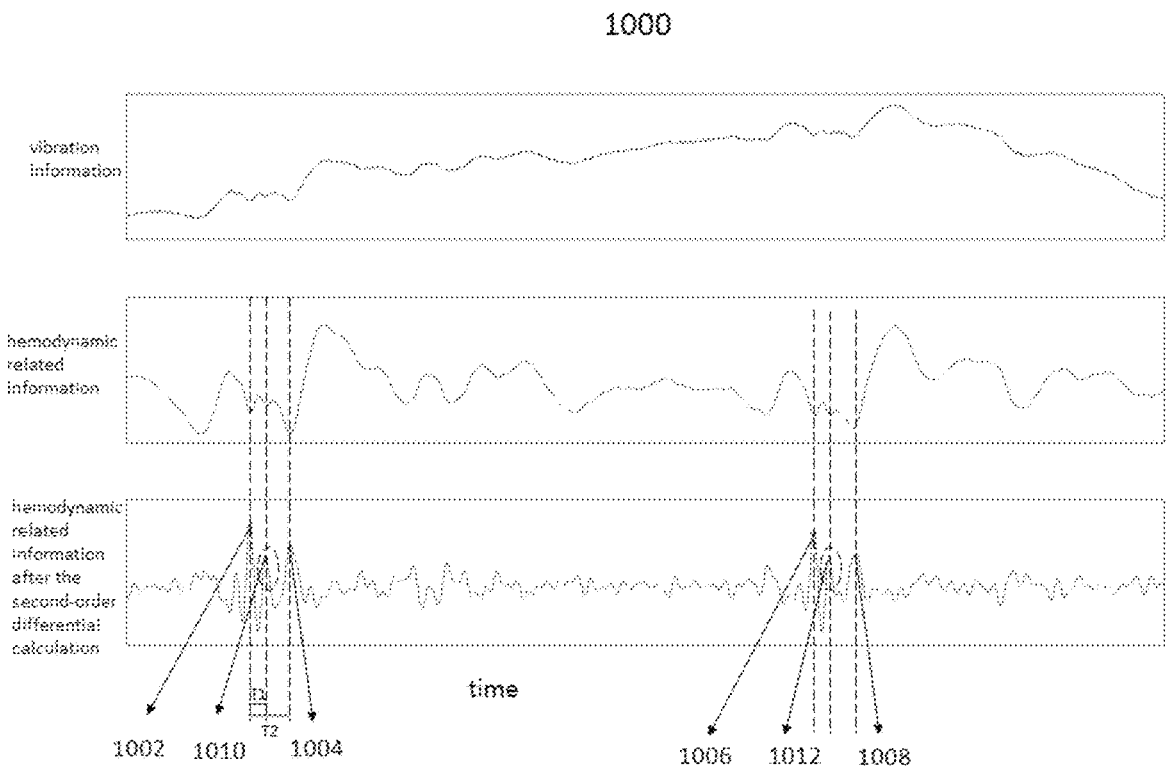
FIG. 10 is an enlarged view of the waveform in area 1000 of FIG. 9.

Step B, performing a feature search on the acceleration signal by the processor 403 to determine the first feature point and the second feature point. The features in the feature search can include, but not limited to, peaks, troughs, wave widths, amplitudes, the maximum value of the function, the minimum value of the function, maximums, minimums, etc. The enlarged view of the signal waveform of the area 800 in FIG. 7 is shown in FIG. 8. In some embodiments, the feature search for the curve 725 can be a peak search, using each cardiac cycle as a search range, the highest peak searched in one cardiac cycle is used as the first feature point, such as point 802. The second highest peak searched in the cardiac cycle is used as the second feature point, such as point 804. The first feature point such as point 806 and the second feature point such as 808 are determined by the feature search in the second cardiac cycle. In some embodiments, due to the different physical conditions of each test subject, such as height, weight, age, fat and thin, etc., the waveforms of the acquired vibration signals are different. As a result, the second highest peak in the cardiac cycle may not correspond to the second feature point. Therefore, when determining the first feature point and the second feature point using the feature search by the processor 403, the PTT confidence interval can also be used to assist the determination. For example, in another embodiment of the present invention, the curve 921 of FIG. 9 is a waveform of vibration information acquired by the fiber-optic sensor device 500 placed at the waist position under the back region of the body corresponding to the bifurcation of the descending aorta and the left and right common iliac arteries of a subject B, where the horizontal axis represents time, and the vertical axis represents the normalized vibration information, which is dimensionless. The enlarged diagram of the curve in the area 1000 of FIG. 9 is shown in FIG. 10. When performing feature search on curve 925, in one cardiac cycle, the highest peak is 1002 as the first feature point, and there are two peaks 1004 and 1010 when searching for the second highest peak. The peak value of these two peaks are similar, which causes interference, and the second feature point can be determined after removing one interference peak. In next cardiac cycle, there is a similar situation, the highest peak is 1006, there are two approximate second highest peaks of 1008 and 1012. Taking the first cardiac cycle as an example, when the interference peak needs to be removed, calculating the time interval T1 between the second highest peak 1010 and the highest peak 1002, and calculating the time interval T2 between the second highest peak 1004 and the highest peak 1002, separately; and then comparing T1 and T2 with the PTT confidence interval, the second highest peak with time interval falling outside the PTT confidence interval is removed as interference peak. The PTT confidence interval discloses the normal range of aortic Pulse Wave Transit Time. The confidence interval can be divided into multiple groups according to factors such as gender, age, height, weight, and the presence or absence of various heart diseases. Each group corresponds to a PTT confidence interval. Therefore, the second highest peak 1010 is removed as the interference peak, and the second highest peak 1004 is determined as the second feature point. In some embodiments, due to differences in the physical fitness or mood of the test subject, in the vibration information continuously captured by the vibration sensor, the first feature point may not correspond to the highest peak in a cardiac cycle, and the second feature point may not corresponding to the second highest peak. In this case, the data of the cardiac cycle can be discarded; or, the wave group can be used for feature search to determine the first feature point and the second feature point.

In some embodiments, other essentially equivalent digital signal processing methods, such as polynomial fitting smoothing filtering, can be performed by the processor 403 to obtain information equivalent to performing a second-order differential calculation.

In some embodiments, in step 611, the processor 403 may obtain the vibration information of the subject from two vibration sensors placed at predetermined positions. The vibration information obtained by one vibration sensor can be used to determine the first feature point, and the vibration information obtained by the other vibration sensor can be used to determine the second feature point. In other embodiments, the processor 403 may use the vibration information obtained by each vibration sensor to determine the first feature point and the second feature point, and then use the vibration information obtained by the two vibration sensors to verify each other to determine and remove some unreasonable information.

In some embodiments, the processor 403 may receive user input from one or more input devices to determine the first feature point and the second feature point of the hemodynamic related information. For example, the external input parameter may be input by the medical staff to the computing device 400 through the input/output port 409 using an input device (for example, a mouse, a keyboard). Medical staff are trained to have the ability to judge feature points from the vibration signal waveform. For example, the enlarged view of curve 725 of FIG. 8, medical staff can manually analyze the waveform, first search the highest peak in a cycle, mark it as the first feature point, and then search the second highest peak within the same cycle after the time corresponding to the highest peak, and mark the second highest peak as the second feature point, and is calibrated using an input device, for example, a mouse is used to select the feature point. Therefore, the first feature point and the second feature point can be determined by the processor 403 based on the input of the medical staff. When there are two or more second highest peaks in the same cycle, the medical staff can calibrate all these second highest peaks, and then the processor 403 uses the PTT confidence interval to exclude and determine the second feature point. Medical staff can also use their own medical knowledge to directly select and mark points in two or more peaks used as the second feature point for subsequent processing.

Step 617: determining an aortic Pulse Wave Transit Time on basis of the first and second feature points. Step 617 is performed by the processor 403. The time corresponding to the first feature point determined in step 615 is regarded as the Aortic Valve Opening Time AVOT, and the time corresponding to the second feature point is regarded as the Pulse Arriving Time PAT. In some embodiments, the first feature point and the second feature point can be located in the same cardiac cycle, so the processor 403 can select a cycle with a relatively stable waveform, and obtain the difference between the Pulse Arriving Time PAT and the Aortic Valve Opening Time AVOT as the Pulse Wave Transit Time. In other embodiments, the processor 403 can select multiple cardiac cycles, for example 20 cardiac cycles, calculate the aortic Pulse Wave Transit Time (i.e., PTT1, PTT2 . . . PTT20) in each cardiac cycle, and then calculate the average value as aortic Pulse Wave Transit Time. In some embodiments, the processor 403 can select a fixed duration, such as 60 seconds, calculate the Pulse Wave Transit Time (i.e., PTT1, PTT2 . . . ) in each cardiac cycle within the duration, and calculate the average value as the Pulse Wave Transit Time. In other embodiments, the processor 403 can also automatically remove data whose Pulse Wave Transit Time is not within a reasonable range and use the average value of the remaining data as the Pulse Wave Transit Time. In other embodiments, the processor 403 can also calculate the Pulse Wave Transit Time in all cycles collected in the test, and calculate the average value thereof as the Pulse Wave Transit Time.

Step 619: obtaining the distance along an aortic path between the vibration sensor and the aorta origin of the supine subject as the pulse wave conduction distance; and determining the Pulse wave velocity based on the pulse wave conduction distance and the Pulse Wave Transit Time. Step 619 is executed by the processor 403. In some embodiments, the pulse wave conduction distance can be measured manually. For example, medical staff can determine the body surface positions corresponding to the aorta origin and the bifurcation of the descending aorta and the left and right common iliac arteries through auscultation or clinical experience, and then use distance measuring tools such as soft rulers, rulers, and scaled lines to measure the pulse wave conduction distance. For another example, the support bed or mattress shown in FIG. 5*b* and FIG. 5*c* may have scale marks, which can be set along the height direction of the body; as shown in FIG. 5*b*, the Z-axis direction, or the opposite direction along the Z-axis, the distance between the fourth thoracic vertebra and the fourth lumbar vertebra of the subject along the Z-axis can be obtained using this scale mark as the approximate value of the aorta pulse wave conduction distance. The medical staff can determine the body surface positions corresponding to the aorta origin and the bifurcation of the descending aorta and the left and right common iliac arteries, and directly read the scale marks as the pulse wave conduction distance of the test subject. The medical staff can then input data through the input device of the system 100, and the processor 403 can thus obtain the pulse wave conduction distance. In other embodiments, the pulse wave conduction distance can be estimated according to a formula. For example, the height, weight, age and other parameters of the test subject can be input through the input device of the system 100, and the processor 403 can estimate the pulse wave conduction distance of the subject according to the formula. For example, the processor 403 can estimate the length of the aorta of the test subject according to the following formula, that is, the aortic pulse wave conduction distance: $L=a+b*(age)+c*(height)+d*(weight)$.

Where, L represents a length of the aorta in centimeters, age in years, height in centimeters, and weight in kilograms. Further, a represents a constant, and b, c, and d are coefficients. The values of a, b, c, d can be obtained by fitting calculation according to the actually-measured aortic length and the age, height, weight, etc. of each tester. In some embodiments, a can be −21.3, b can be 0.18, c can be 0.32, and d can be 0.08.

Step 621: sending at least one of the Pulse Wave Transit Time and the Pulse Wave Velocity to one or more output device. Step 621 is performed by the processor 403. For example, the Pulse Wave Transit Time can be sent to the output device 109 in the system 100 for output. The output device 109 can be a display device, such as a mobile phone, which can display the Pulse Wave Transit Time in graphics or text. The output device 109 can be a printing device, which prints the measurement report of the pulse wave conduction parameters. The output device 109 can be a voice broadcast device, which outputs pulse wave conduction parameters in voice. In some embodiments, the processor 403 can send the Pulse Wave Transit Time and/or the Pulse Wave Velocity to an output device via a wireless network, for example, the output device is a mobile phone. In other embodiments, the processor 403 can directly send the Pulse Wave Transit Time and/or the Pulse Wave Velocity to the output device through a cable. For example, the output device is a display, which can be connected to the sensor device through a cable.

In some embodiments, the steps of the method 600 can be performed in order, in other embodiments, the steps of the method 600 can be performed not in order, or can be performed simultaneously. For example, after step 617, determining an aortic Pulse Wave Transit Time on basis of the first and second feature points; the steps: step 619, obtaining the distance along the aortic path between the vibration sensor and the aorta origin of the supine subject as the pulse wave conduction distance; and determining the Pulse wave velocity based on the pulse wave conduction distance and the Pulse Wave Transit Time; and step 621, sending at least one of the Pulse Wave Transit Time and the Pulse Wave Velocity to one or more output device; may be performed simultaneously. In addition, in some embodiments, one or more steps of the method 600 can be removed. For example, step 619 and step 621 may not be performed. In other embodiments, other operation steps may also be added to the method 600.

A computer-readable storage medium provided in the embodiment of the present invention, the computer-readable storage medium have a computer program stored thereon, and which when being executed by a processor, cause the processor to perform method or steps of the pulse wave conduction parameter measurement.

Figure 11:
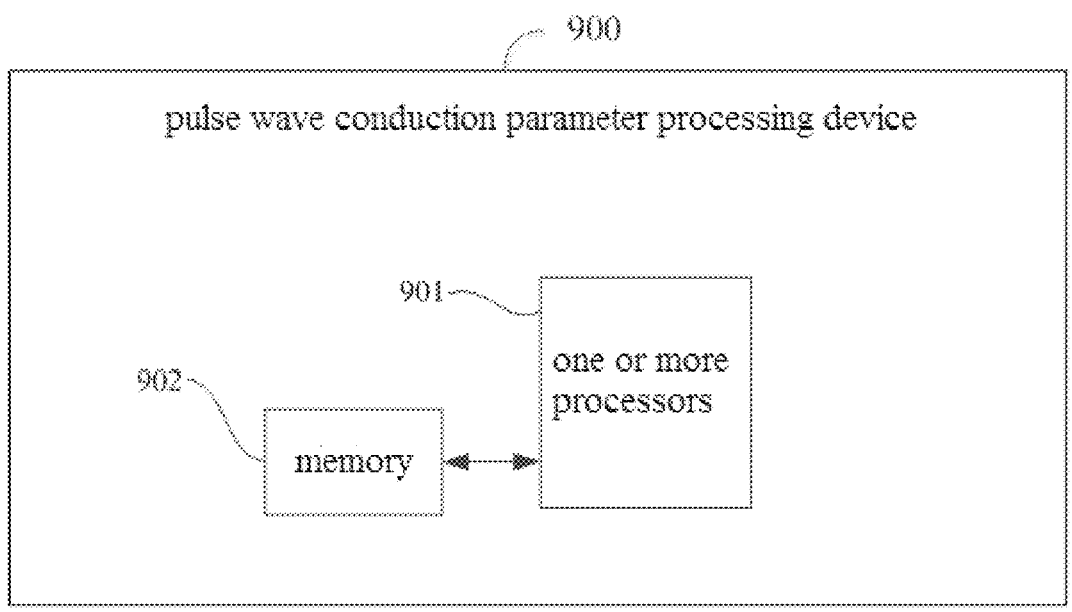
FIG. 11 is a block diagram of a pulse wave conduction parameter processing device in accordance with some embodiments of the present invention.

FIG. 11 shows a block diagram of a pulse wave conduction parameter processing device provided in an embodiment of the present invention. A pulse wave conduction parameter processing device 900 includes: one or more processors 901, a memory 902, and one or more computer programs, wherein the processor 901 and the memory 902 are connected by a bus. The one or more computer programs are stored in the memory 902 and configured to be executed by the one or more processors 901, which when being executed by the one or more processors 901, cause the one or more processors 901 to perform method or steps of the pulse wave conduction parameter measurement described in the above embodiments.

The aorta of the human body passes through the thoracic cavity and abdominal cavity of the body and is not a superficial artery. The traditional method of measuring the pulse wave conduction parameter of the superficial artery is not suitable for the measurement of the pulse wave conduction parameter of the aorta. In the present invention, the vibration information of the subject is obtained from one or more vibration sensors configured to be placed in predetermined positions; hemodynamic related information is generated based on the vibration information; the first feature point and the second feature point of the hemodynamic related information is determined, wherein the first feature point is a point related to the aortic valve opening time of the subject, and the second feature point is a point related to the Pulse Arriving Time of the subject. The Pulse Wave Transit Time of the subject can be obtained based on the first feature point and the second feature point, thereby Pulse Wave Velocity can be obtained, and used to evaluate the elasticity of the artery. Therefore, using the method for measuring human aortic pulse wave conduction parameters provided in the present invention, the measurement can be performed only needs the test subject to lie on the measurement device or wear the measurement device without direct contact; the measurement accuracy is high, simple to operate, can improve the comfort to the test subject, and can be applied to scenes such as hospitals and homes.

It should be noted that the above description is only a specific embodiment of this invention, and should not be regarded as the only embodiment. Obviously, for professionals in the field, after understanding the content and principles of the application, they can make various amendments and changes in form and details without departing from the principles and structure of the invention, but these amendments and changes are still within the protection scope of the claims of the present invention.

What is claimed is:

1. A pulse wave conduction parameter measurement method, comprising steps of:
continuously acquiring vibration information of a supine subject through a fiber-optic strain sensor which is controlled by a processor, wherein the fiber-optic strain sensor comprises an optical fiber and a mesh layer in a sensor pad, a light source and a receiver coupled to both ends of the optical fiber, and a control and processing module connected to the light source, the receiver and the processor; wherein the continuously acquiring comprises steps of:
continuously applying force by body vibrations caused by the subject' respiration, heart contraction and pulse waves propagating along blood vessel, on the sensor pad; wherein the subject is in a supine resting state on the sensor pad, the fiber-optic strain sensor is configured to be placed under any position of the back and the waist corresponding to a descending aorta between the fourth thoracic vertebra and the fourth lumbar vertebra, the body vibrations include a first body vibration caused by the aortic valve opening and blood impacting the aortic arch to generate the pulse waves, and a second body vibration caused by the pulse waves propagating along the blood vessel; the first body vibration and the second body vibration are successive in a same cardiac cycle;

generating micro-bending of the optical fiber and changes in intensity of light transmitted through the optical fiber under the force distributed around the optical fiber through the mesh layer;

receiving and processing, on the control and processing module, data of the changes in intensity of light transmitted through the optical fiber from the receiver; and receiving and processing, on the processor, the processed data from the control and processing module and determining the vibration information, wherein the vibration information includes vibration information caused by breathing, and vibration information caused by the successive first vibration and second vibration in the same cardiac cycle;

generating, executing on the processor, hemodynamic related information by means of filtering the vibration information in different frequencies and scaling the filtered vibration information; comprising steps of:

filtering the vibration information below 1 Hz to remove the vibration information caused by breathing;

filtering power frequency noise in the vibration information using a power frequency filter; and scaling the filtered vibration information according to a signal dynamic range to obtain the hemodynamic related information;

performing, executing on the processor, a second-order differential calculation on the hemodynamic related information to obtain a time-domain waveform of the second-order differential with a horizontal axis representing time;

performing, executing on the processor, a feature search on the time-domain waveform of the second-order differential to determine a first feature point and a second feature point;

wherein the first feature point is related to an aortic valve opening time (AVOT) of the subject, and is a first highest peak in one cardiac cycle of the time-domain waveform of the second-order differential, and the second feature point is related to a Pulse Arriving Time (PAT) of the subject, and is a second highest peak in the same cardiac cycle;

determining, executing on the processor, a Pulse Wave Transit Time (PTT) of the subject based on the first feature point and the second feature point, which is a difference between the PAT and the AVOT;

determining, executing on the processor, a Pulse Wave Velocity (PWV) based on a pulse wave conduction distance and the PTT, where the pulse wave conduction distance is a distance along an aortic path between the fiber-optic strain sensor and the aorta origin of the supine subject; and assessing, according to the PWV, a degree of arterial elasticity, wherein a higher stiffness of the blood vessel corresponds to a faster PWV.

2. The method of claim 1, wherein said fiber-optic strain sensor comprises:

the optical fiber, disposed substantially in one plane;

the light source, coupled to one end of the optical fiber;

the control and processing module;

the receiver, coupled to the other end of the optical fiber, and configured to sense the changes in intensity of light transmitted through the optical fiber; and the mesh layer for supporting the optical in the plane, composed of meshes with openings, in contact with surface of the optical fiber, and used to disperse the force that would have been applied to a point of the optical fiber and distribute the force to the optical fiber around the point.

3. The method of claim 2, wherein the optical fiber is a multi-mode optical fiber or a single-mode optical fiber; the optical fiber is arranged in a serpentine structure, or a U-shape, or a looped structure; where the looped structure is formed by one optical fiber arranged into a plurality of equal-sized loops disposed substantially in one plane, and each loop within the looped structure is partially overlapping yet laterally offset from neighboring loops.

4. The method of claim 2, wherein the fiber-optic strain sensor further comprises a lower cover and an upper cover; the lower cover and the upper cover are configured to surround the optical fiber and the mesh layer; and the lower cover, the optical fiber, the mesh layer, and the upper cover are laminated into the sensor pad.

5. The method of claim 1, wherein the fiber-optic strain sensor is configured to be placed under the waist region corresponding to the bifurcation of the descending aorta and the left and right common iliac arteries of the subject.

6. The method of claim 1, wherein for determining the first feature point and the second feature point, a PTT confidence interval is used to remove interference peaks.

7. A non-transitory computer-readable storage medium, wherein the non-transitory computer-readable storage medium has a set of computer-executable program instructions stored thereon, and the set of computer-executable program instructions being executed by the processor, cause the processor to perform the steps of the method of claim 1.

8. A pulse wave conduction parameter measurement method, comprising steps performing by one or more processors:

providing one or more vibration sensors connected with the one or more processors, where the one or more vibration sensors comprise a fiber-optic strain sensor and/or an acceleration sensor; if more than one vibration sensors are provided, stacking and placing the vibration sensors at a same position so as to acquire the vibration information of a same body section;

continuously acquiring vibration information of a supine subject by the one or more vibration sensors configured to be placed under any position of the back and the waist corresponding to the descending aorta between the fourth thoracic vertebra and the fourth lumbar vertebra;

generating a time-domain waveform of hemodynamic related information by means of filtering and scaling the vibration information, comprising steps of:

filtering the vibration information below 1 Hz for filtering out the vibration information caused by breathing;

filtering power frequency noise using a power frequency filter; and scale the filtered vibration information according to a signal dynamic range to obtain the hemodynamic related information;

for the fiber-optic strain sensor, performing a second-order differential calculation on the hemodynamic related information to obtain a time-domain waveform of the second-order differential;

determining a first feature point and a second feature point by means of feature search, wherein, for the fiber-optic strain sensor, perform a feature search on the time-domain waveform of the second-order differential; for the acceleration sensor, perform a feature search on the time-domain waveform of hemodynamic related information; the first feature point is related to an aortic valve opening time (AVOT) of the subject, and is a first highest peak in one cardiac cycle of the time-domain waveform, and the second feature point is related to a Pulse Arriving Time (PAT) of the subject, and is a second highest peak in the same cardiac cycle;

determining a Pulse Wave Transit Time (PTT) of the subject based on the first feature point and the second feature point, which is a difference between the PAT and the AVOT;

determining a Pulse Wave Velocity (PWV) based on a pulse wave conduction distance and the PTT, where the pulse wave conduction distance is a distance along an aortic path between the vibration sensor and the aorta origin of the supine subject; and assessing, according to the PWV, a degree of arterial elasticity, wherein a higher stiffness of the blood vessel corresponds to a faster PWV.

9. The method of claim 8, wherein the one or more vibration sensors include two vibration sensors stacked and placed at the same position so as to acquire the vibration information of the same body section; where the vibration information obtained by a first vibration sensor is used to determine the first feature point, and the vibration information obtained by a second vibration sensor is used to determine the second feature point; or, using the vibration information obtained by the first vibration sensor and the second vibration sensor to determine the first feature point and the second feature point, and then using the vibration information obtained by the first vibration sensor and the second vibration sensor to verify each other.

10. A pulse wave conduction parameter measurement system, comprising:
one or more vibration sensors for acquiring vibration information of a supine subject, comprising a fiber-optic strain sensor and/or an acceleration sensor;
a pulse wave conduction parameter processing device, connected to the one or more vibration sensors; and
an output device, connected with the pulse wave conduction parameter processing device for outputting pulse wave conduction parameters of the subject;
wherein the pulse wave conduction parameter processing device comprises:
one or more processors;
a memory; and
one or more computer programs stored on the memory and configured to be executed by the one or more processors;
wherein the one or more computer programs being executed by the one or more processors cause the one or more processors to perform a pulse wave conduction parameter measurement method, comprising steps of:
continuously acquiring vibration information of the supine subject from the one or more vibration sensors configured to be placed under any position of the back and the waist corresponding to the descending aorta between the fourth thoracic vertebra and the fourth lumbar vertebra; where the one or more vibration sensors are connected with the one or more processors and are stacked and placed under a same position of the body section;
generating a time-domain waveform of hemodynamic related information by means of filtering and scaling the vibration information; comprising steps of:
filtering the vibration information below 1 Hz for filtering out the vibration information caused by breathing;
filtering power frequency noise using a power frequency filter;
scale the filtered vibration information according to a signal dynamic range to obtain the hemodynamic related information;
for the fiber-optic strain sensor, performing a second-order differential calculation on the hemodynamic related information to obtain a time-domain waveform of the second-order differential;
determining a first feature point and a second feature point by means of feature search, wherein, for the fiber-optic strain sensor, perform a feature search on the time-domain waveform of the second-order differential; for the acceleration sensor, perform a feature search on the time-domain waveform of hemodynamic related information; the first feature point is related to an aortic valve opening time (AVOT) of the subject, and is a first highest peak in one cardiac cycle of the time-domain waveform; and the second feature point is related to a Pulse Arriving Time (PAT) of the subject, and is a second highest peak in the same cardiac cycle;
determining a Pulse Wave Transit Time (PTT) of the subject based on the first feature point and the second feature point, which is a difference between the PAT and the AVOT;
determining a Pulse Wave Velocity (PWV) based on a pulse wave conduction distance and the PTT where the pulse wave conduction distance is a distance along an aortic path between the vibration sensor and the aorta origin of the supine subject; and
assessing, according to the PWV, a degree of arterial elasticity, wherein a higher stiffness of the blood vessel corresponds to a faster PWV.

11. The system of claim 10, wherein the output device is connected with the one or more vibration sensors for outputting the acquired vibration information of the subject.

12. The system of claim 10, further comprising:
a storage device connected with the one or more vibration sensors and/or the pulse wave conduction parameter processing device for storing the acquired vibration information and/or the pulse wave conduction parameters of the subject.

13. The system of claim 12, wherein the pulse wave conduction parameter processing device, the output device and the storage device are set in a mattress as a whole.

* * * * *